US00PP35485P3

(12) United States Plant Patent
Kordes

(10) Patent No.: US PP35,485 P3
(45) Date of Patent: Nov. 21, 2023

(54) MINIATURE ROSE PLANT NAMED 'KORPOT119'

(50) Latin Name: *Rosa hybrida*
Varietal Denomination: KORpot119

(71) Applicant: W. KORDES' SÖHNE Rosenschulen GmbH & Co KG, Klein Offenseth-Sparrieshoop (DE)

(72) Inventor: Wilhelm Alexander Kordes, Klein Offenseth-Sparrieshoop (DE)

(73) Assignee: W. KORDES' SÖHNE ROSENSCHULEN GMBH & CO KG, Klein Offenseth-Sparrieshoop (DE)

( * ) Notice: Subject to any disclaimer, the term of this patent is extended or adjusted under 35 U.S.C. 154(b) by 55 days.

(21) Appl. No.: 18/088,926

(22) Filed: Dec. 27, 2022

(65) Prior Publication Data

US 2023/0210031 P1 Jun. 29, 2023

Related U.S. Application Data

(60) Provisional application No. 63/294,117, filed on Dec. 28, 2021.

(51) Int. Cl.
*A01H 5/02* (2018.01)
*A01H 6/74* (2018.01)

(52) U.S. Cl.
USPC ..... Plt./119
CPC ..... *A01H 6/749* (2018.05)

(58) Field of Classification Search
USPC ..... Plt./119
CPC ..... A01H 6/749; A01H 5/02
See application file for complete search history.

(56) References Cited

U.S. PATENT DOCUMENTS

PP24,207 P2 2/2014 Kordes
PP27,162 P2 9/2016 Kordes

*Primary Examiner* — Keith O. Robinson
(74) *Attorney, Agent, or Firm* — Panitch Schwarze Belisario & Nadel LLP; Stephany G. Small; Travis W. Bliss

(57) ABSTRACT

A new and distinct variety of miniature rose plant, referred to by its cultivar name, 'KORpot119', is described. The new variety forms in abundance on a substantially continuous basis attractive, orange-colored blossoms. The vegetation is vigorous and the growth habit is compact. Attractive dark green, semi-glossy foliage is formed. Additionally, the new variety is particularly well suited for growing as distinctive ornamentation in the landscape.

2 Drawing Sheets

Figure 1:
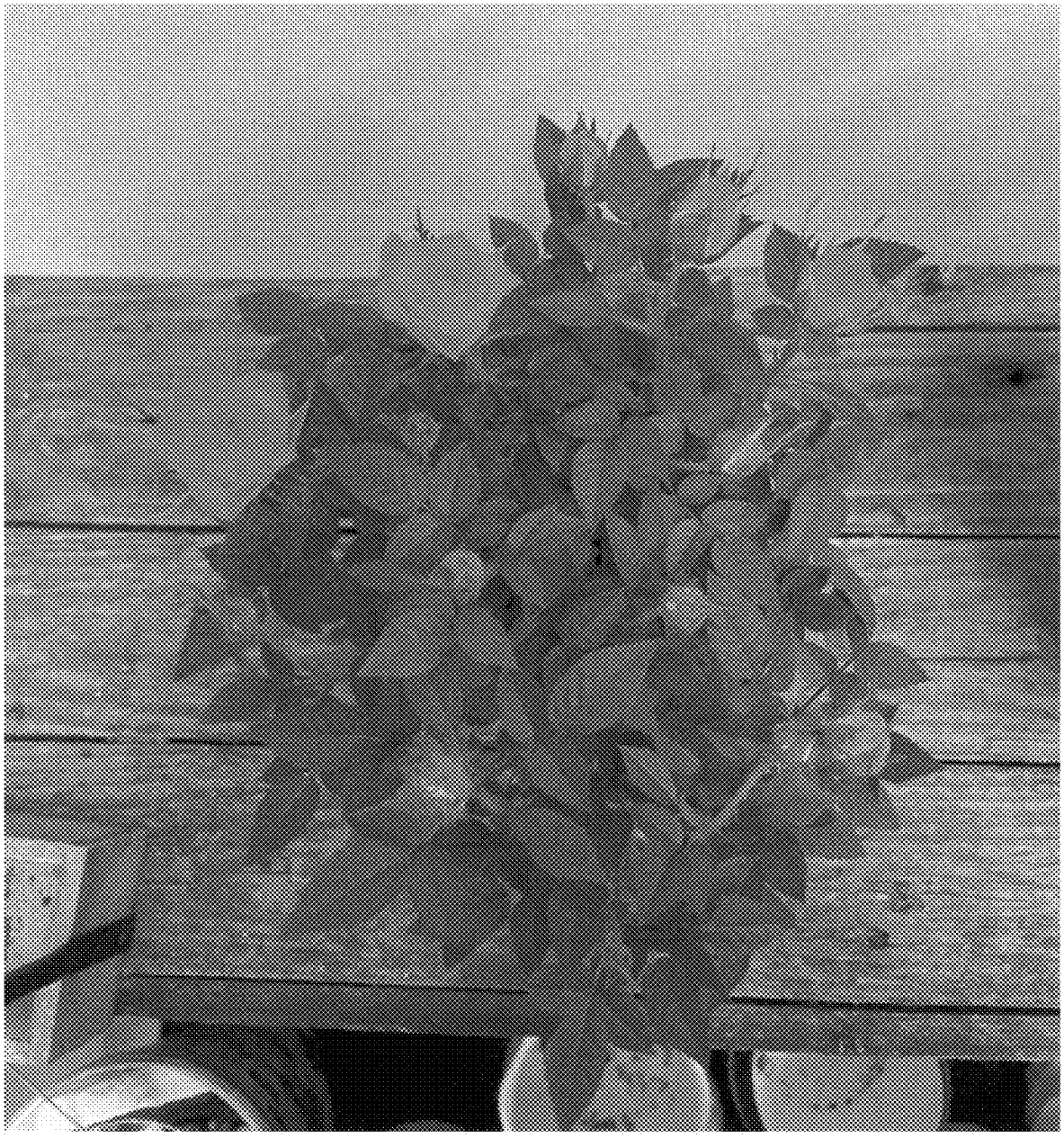

Latin name of genus and species of plant claimed: *Rosa hybrida.*

Variety denomination: 'KORpot119'.

STATEMENT REGARDING PRIOR DISCLOSURES BY THE INVENTOR

The first offer for sale of the new variety was March 2021 in the United States of America. The first offer for sale of the new variety was by the inventor or another who obtained the new variety directly or indirectly from the inventor. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The new variety of miniature rose plant of the present invention was created by controlled breeding in 2015 at Offenseth-Sparrishoop, Germany by artificial pollination wherein two parents were crossed which previously had been studied in the hope that they would contribute the desired characteristics. The female parent (i.e., the seed parent) of the new variety was the 'RUId155a' (not patented). The male parent (i.e., the pollen parent) of the new variety was the 'KORpot050' variety (U.S. Plant Pat. No. 27,162).

The parentage of the new variety can be summarized as follows:

'RUId155a' x 'KORpot050'

The seeds resulting from the above pollination were sown and small plants were obtained which were physically and biologically different from each other. Selective study resulted in the identification of a single plant of the new variety.

The new variety has been found to undergo asexual propagation at Klein Offenseth-Sparrieshoop, Germany by a number of routes such as vegetative cuttings. Asexual propagation techniques in Klein Offenseth-Sparrieshoop, Germany, such as vegetative cuttings, have shown that the characteristics of the new variety are homogeneous, stable, and strictly transmissible by such asexual propagation from one generation to another. Accordingly, the new variety undergoes asexual propagation in a true-to-type manner.

SUMMARY OF THE INVENTION

It was found that the new variety of miniature rose plant of the present invention possesses the following combination of characteristics:

(a) forms attractive, orange-colored blossoms,
(b) exhibits a compact growth habit,
(c) forms vigorous vegetation, and
(d) forms attractive ornamental semi-glossy foliage.

The new variety well meets the needs of the horticultural industry. It can be grown to advantage as attractive ornamentation in parks, gardens, public areas, and residential landscapes. Accordingly, it is particularly well suited for growing in the landscape.

The new variety can be readily distinguished from its ancestors. More specifically, the 'RUId155a' (i.e., the seed parent) displays a less compact growth habit and provides a less rounded flower shape compared to the new variety. Additionally, the 'KORpot050' variety (i.e., the pollen parent) displays an orange-red colored flower and provides a larger flower compared to the new variety. Moreover, the new variety can be readily distinguished from non-parental related similar varieties. For example, 'KORpot021' (U.S. Plant Pat. No. 24,207) displays less apricot/orange colored flowers, provides a smaller flower size, and exhibits a shorter growth habit compared to the new variety.

The new variety has been named the 'KORpot119' variety.

BRIEF DESCRIPTION OF THE PHOTOGRAPHS

The accompanying photographs show, as nearly true as it is reasonably possible to make the same in a color illustration of this character, typical specimens of the new variety and blossoms of the new variety. The illustrated rose plants of the new variety were approximately twelve weeks of age and were grown indoors in 4 inch containers on their own roots at Surrey, British Columbia, Canada.

FIG. 1—illustrates a specimen of the plant displaying flowers at varying points of opening—top view.

Figure 2:
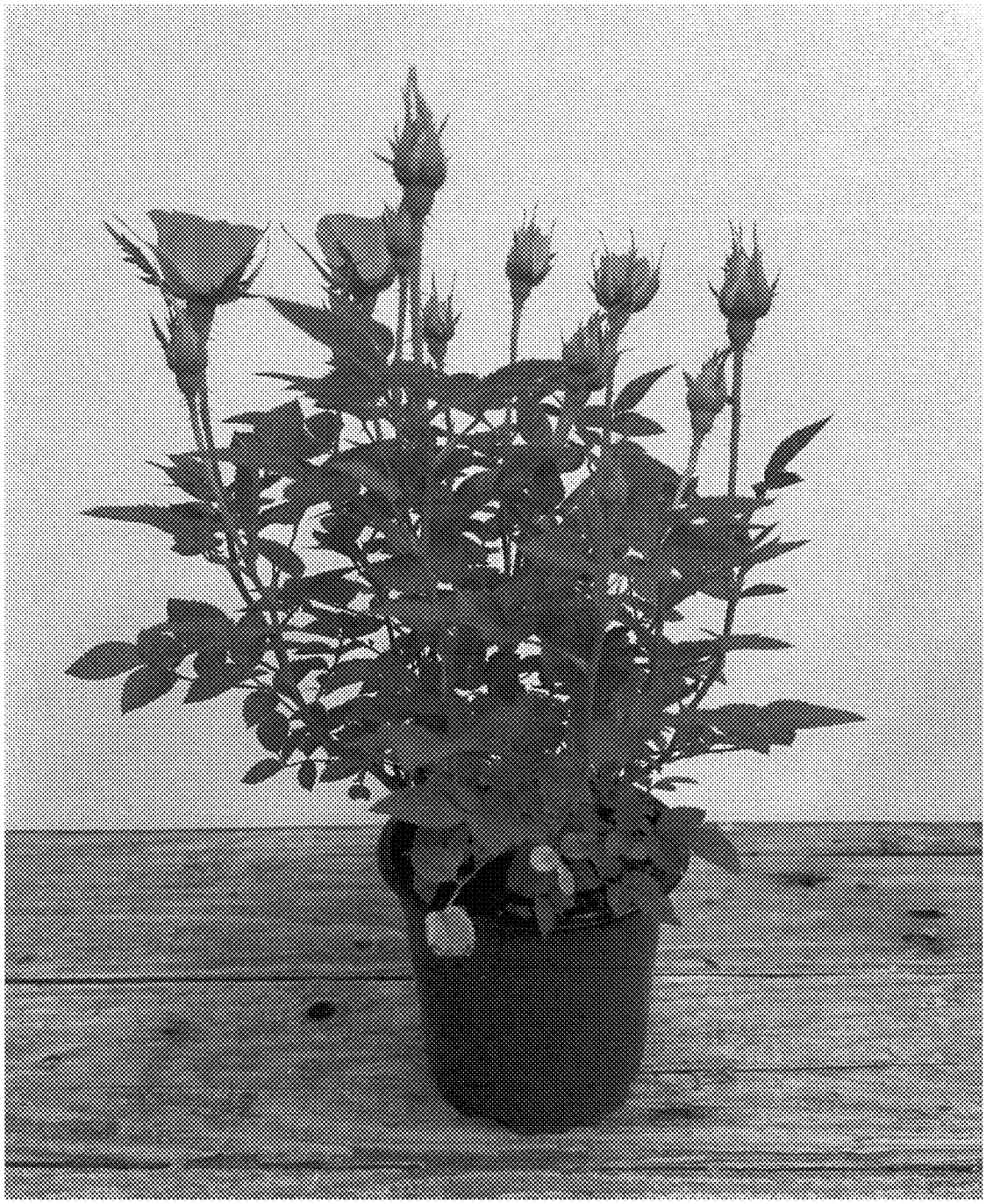

FIG. 2—illustrates a specimen of the plant displaying flowers at varying points of opening—side view.

DETAILED BOTANICAL DESCRIPTION

The chart used in the identification of colors is that of The Royal Horticultural Society (R.H.S. Colour Chart, 2015 edition). The terminology which precedes reference to the chart has been added to indicate the corresponding color in more common terms. The description is based on a one-year-old specimen of the new variety, observed during November, while growing on its own roots in a greenhouse in a one-gallon container in Cochranville, Pa.

Botanical classification: *Rosa hybrida* cultivar KORpot119.

Commercial classification: Miniature Rose.

Plant:

*Height*.—Approximately up to 35.0 cm.

*Width*.—Approximately up to 32.0 cm.

*Habit*.—Compact.

Branches:

*Stem color*.—Commonly near Green Group 143A.

*Length*.—Main stems: approximately 35.0 cm on average. — secondary stems: approximately 9.0 to 12.0 cm on average.

*Texture*.—Glabrous.

*Thorns*.—Amount moderate. — young thorns: length is approximately 3.0 mm on average; width is approximately 1.0 mm at point of attachment; and color is commonly near Greyed-Red Group 179C.

Leaflets:

*Number*.—3, 5, and 7.

*Shape*.—Ovate; apex is acute; and base is rounded.

*Arrangement*.—Odd-pinnate.

*Venation pattern*.—Reticulate.

*Margin*.—Serrate.

*Glossiness of upper side*.—Semi-glossy.

*Texture*.—Upper surface: smooth. — under surface: smooth.

*Size*.—Terminal leaflet: length is approximately 3.0 cm on average; width is approximately 2.0 cm on average. — lower leaflets: length is approximately 2.0 cm on average; width is approximately 1.3 cm on average. — 5-Leaflet leaf: length is approximately 6.0 cm on average; width is approximately 4.6 cm on average.

Foliage:

*Young foliage*.—Upper surface color: commonly near Green Group 137A with indistinguishable venation. — under surface color: commonly a blend of near Green Group 1386 and Green Group 138C with venation near Green Group 138C.

*Old foliage*.—Upper surface color: commonly near Green Group 137A with indistinguishable venation. — under surface color: commonly near Green Group 1386 with venation near Green Group 139C.

*Petiole*.—Texture: upper surface is smooth; under surface is mostly smooth with sparse prickles. — upper surface color: commonly near Green Group 137A. — under surface color: commonly near Green Group 137B.

*Rachis*.—Upper surface color: commonly near Green Group 137A. — under surface color: commonly near Green Group 137B.

*Stipules*.—Length: approximately 4.0 mm on average. — width: approximately 1.0 mm on average. — margin: entire to erose. — upper surface: color commonly near Green Group 137A. — lower surface color: commonly near Green Group 138B.

Inflorescence:

*Number of flowers*.—About 7 blooms on average on a plant at once.

*Number of blossoms per stem or in a cluster*.—Typically 1 and 3 blooms per stem on average.

*Peduncle*.—Color: commonly near Green Group 138A. — diameter: approximately 3.0 mm on average. — length: approximately 4.0 cm on average. — surface texture: glabrous. — strength: strong.

*Sepals*.—Number: 5. — upper surface color and texture: commonly near Green Group 138A, covered in short pubescence. — under surface color and texture: commonly near Green Group 138A, puberulent. — size: length is approximately 2.5 cm on average; width is approximately 8.0 mm on average. — margin: entire with extension on two or three sepals measuring 7.0 mm in length and 2.0 mm in width. — shape: lanceolate. — apex: acute to aristate. — base: truncate or flat as it joins the receptacle.

*Buds*.—Shape: globular. — size: length is approximately 2.0 cm on average; width is approximately 2.0 cm on average. — color (when opening): commonly near Red Group 40A.

*Flower*.—Form: double, cuplike. — profile: flat. — diameter: approximately 5.0 cm on average. — height: approximately 2.0 cm on average. — duration: on the plant approximately 18 days. — petal color when first and fully opened: upper surface is commonly near Red Group 40A with a basal spot of near Yellow Group 12B; under surface is commonly near Red Group 40A with basal spot of near Yellow Group 12B. — petal color when fading: upper and under surfaces are commonly near Red Group 45A with hint of Yellow Group 12C. — petal texture of upper and lower surfaces: glabrous.

*Fragrance*.—None noticeable.

*Petal*.—Number: 18 on average. — drop: average for the type. — length: inner petals are approximately 1.5 cm on average and outer petals are approximately 2.5 cm on average. — width: inner petals are approximately 6.0 mm on average and outer petals are approximately 3.0 cm on average. — overall shape: broadly obovate. — margin: entire. — apex shape: rounded to cuspidate. — base shape: rounded to cuneate.

*Petaloids*.—Number commonly 5 per flower. — color upper and under surfaces: commonly near Red Group 40A with a basal spot of near Yellow Group 12A. — length: approximately 5.0 mm on average. — width: approximately 3.0 mm on average. — texture: smooth. — margins: variable, entire to erose. — shape: rounded and mostly curving inward. — apex: round. — base: cuneate.

*Stamen*.—Number: approximately 80. — anthers: number is approximately 80; color is commonly near Yellow Group 11C; length is approximately 1.5 mm on average; and shape is oval. — filaments: length is approximately 1.5 mm on average and color is commonly near Yellow Group 13B.

*Pistils*.—Arrangement: separate and free. — number: approximately 96. — style: length is approximately 5.0 mm and color is commonly near Green-Yellow Group 1B at the base, transitioning to near Red Group 45A at the apex. — stigma: diameter is commonly less than 1.0 mm; shape is fan shaped; and color is commonly near Green-Yellow Group 1B.

*Receptacle*.—Diameter: approximately 1.0 cm on average. — shape: urn shaped. — color: commonly near Green Group 143A. — surface texture: smooth.

*Pollen*.—None observed.

*Hips/seed*.—None observed.

Development:

*Vegetation*.—Dark green, vigorous, and strong.

*Blossoming*.—Abundant and substantially continuous.

*Resistance to diseases*.—Good resistance for powdery mildew (*Sphaerotheca pannosa*) disease under normal greenhouse growing conditions in Cochranville, Pa.

*Hardiness*.—Unknown.

The new 'KORpot119' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of miniature rose plant named 'KORpot119' characterized by the following combination of characteristics:

(a) forms attractive, orange-colored blossoms, (b) exhibits a compact growth habit, (c) forms vigorous vegetation, and (d) forms attractive ornamental semi-glossy foliage;

substantially as herein shown and described.

* * * * *